United States Patent [19]
Ferro et al.

[11] Patent Number: 5,676,965
[45] Date of Patent: Oct. 14, 1997

[54] USE OF POLYDEOXYRIBONUCLEOTIDES IN DIABETIC NEUROPATHIES

[75] Inventors: Laura Ferro; Ennio Lanzarotti, both of Milan, Italy

[73] Assignee: Crinos Industria Farmacobiologica S.p.A., Villa Guardia, Italy

[21] Appl. No.: 505,148

[22] Filed: Jul. 21, 1995

[30] Foreign Application Priority Data

Aug. 3, 1994 [IT] Italy .................... MI94A1687

[51] Int. Cl.⁶ .................. A61F 2/00; A61K 9/16; A61K 9/20; A61K 9/48
[52] U.S. Cl. .......... 424/423; 424/451; 424/464; 424/489; 514/866
[58] Field of Search .................. 424/423, 464, 424/451, 489; 514/866

[56] References Cited

U.S. PATENT DOCUMENTS 5,223,609  6/1993  Fedeli et al. .................. 536/23.1

FOREIGN PATENT DOCUMENTS

| | | |
|---|---|---|
| 0 513 513 A1 | 11/1992 | European Pat. Off. . |
| 0 558 833 A2 | 9/1993 | European Pat. Off. . |
| 0 582 330 A1 | 2/1994 | European Pat. Off. . |
| WO 87/06235 | 10/1987 | WIPO . |

OTHER PUBLICATIONS

Y. Okamiya et al., "Antihypertensive Effect of the New Calcium Antagonist (±)-3(Benzylmethylamino)-2, 2-dimethylpropyl-methyl-4-(2-fluoro-5-Nitrophenyl)-1, 4-dihydro-2,6-dimethyl3,5-pyridinedicarboxylate Hydrochloride in Rats", Dept. of Pharmacology, Teijin Institute for Bio-Medical Research II, Tokyo (Japan) 1992.

Mark A. Yorek et al., "Restoration of Na⁺-K⁺ Pump Activity and Resting Membrane Potential by myo-Inositol Supplementation in Neuroblastoma Cells Chronically Exposed to Glucose or Galactose", Diabetes, vol. 40, Feb. 1991.

*Primary Examiner*—Thurman K. Page
*Assistant Examiner*—James M. Spear
*Attorney, Agent, or Firm*—Nikaido Marmelstein Murray & Oram LLP

[57] ABSTRACT

A pharmaceutical composition comprising a polydeoxyribonucleotide of random sequence formula is disclosed, and $$P_y, (dAp)_w, (dGp)_x, (dTp)_y, (dCp)_z$$

wherein
- $P_y$ is 1–5 phosphoric radicals,
- $(dAp)_w$ is 12–24 deoxyadenylic monomers,
- $(dGp)_x$ is 10–20 deoxyguanylic monomers,
- $(dTp)_y$ is 13–26 deoxythymidylic monomers, and
- $(dCp)_z$ is 10–20 deoxycytidylic monomers;

wherein the polydeoxyribonucleotide has:
- a homogenous anodic mobility in electrophoresis,
- an extinction coefficient $E^1_{1\ cm}$ at 260±1 nm=220±10,
- an extinction coefficient $E_{230}/E_{260}=0.45\pm0.04$,
- a molar extinction coefficient (referred to phosphorous), $\epsilon(P)=7750\pm500$,
- a rotary power $[\alpha]^{20°}_D=53°\pm6$, and
- a reversible hyperchromicity as percent in native DNA h=15±5, in combination with a pharmaceutically acceptable carrier or diluent. A method of treating or preventing a diabetic neuropathy using the polydeoxyribonucleotide is also shown.

5 Claims, 1 Drawing Sheet

USE OF POLYDEOXYRIBONUCLEOTIDES IN DIABETIC NEUROPATHIES

The object of the present invention is the use of the polydeoxyribonucleotides disclosed in the European patent n. 263155 in the prophylaxis and therapy of diabetic neuropathies.

Said polydeoxyribonucleotides are obtained by chemical depolymerization of deoxyribonucleic acid extracted from animal organs and in said European patent they have been defined from a chemical point of view as it follows:

Random sequence formula:

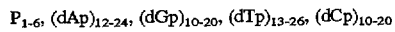

$P_{1-6}$, $(dAp)_{12-24}$, $(dGp)_{10-20}$, $(dTp)_{13-26}$, $(dCp)_{10-20}$

Wherein P, dAp, dGp, dTp, dGp have the meaning given in the patent.

Electrophoresis:homogeneous band shifted towards the anode.

Extinction coefficient $E^{1\%}_{1\,cm}$ at $260\pm1$ nm$=220\pm10$.

Extinction coefficient $E_{230}/E_{260}=0,45\pm0,04$.

Molar extinction coefficient (referred to phosphorous) $E(P)=7750\pm500$.

Rotatory power $[\alpha]^{20°}_D = +53°\pm6°$.

Reversible hyperchromicity as % native DNA $h=15\pm5$.

For that it concerns the therapeutic use that constitutes the object of the instant invention, the state of the art provides the following information on the activity in peripheral neuropathies of compounds that may be reputed to have some relation with the above referred to polydeoxyribonucleotides:

The paper of B. Wattig et Alii "Enhancement of nerve fiber regeneration by nucleotides after peripheral nerve crush damage" Arzneim. Forsch./Drug Res. 42 (II) 9 1992 discloses that in an experimental model wherein the sciatic nerve of rats underwent to mechanical compression (nerve crush damage), the subsequent prolongued administration i.m. of a mixture of uridine monophosphate and citidine monophosphate brought about a substantial recovery of nerve conduction, with concomitant regrowth of nerve fibers. Said otherwise, this paper makes a clear hint to the activity of said nucleotides in peripheral neuropathies.

From E.P. n. 513513 and E.P.A. 93202089.4 (publication number n. 582330 ) respectively it is known the use in diabetic neuropathies and in peripheral acute neuropathies of glycosaminoglycans, that are polymers of extractive origin as are the polydeoxyribonucleotides hereabove mentioned.

The following substantial differences can be however accounted for between the above prior art and the object of the instant invention:

For what it concerns the aforementioned paper of B. Wattig et Alii it must be observed that within the field of peripheral neuropathies the polydeoxyribonucleotides of E.P.263155 have been instead found to be devoid of activity in acute peripheral neuropathies, as it will be further on demonstrated with the pharmacological test of the experimental lesion of sciatic nerve.

Said latter test had formerly been used to evidence glycosaminoglycan activity in acute peripheral neuropathies (ref. E.P.A. n 93202089.4).

On the basis of the above findings it can be desumed that polydeoxyribonucleotides don't exhibit a uniform activity in the field of peripheral neuropathies. In fact said compounds although ineffective in acute peripheral neuropathies, in the present invention have been demonstrated to be valuable active principles in the treatment of diabetic neuropathies.

It is reputed that these findings are to be considered fully unforeseeable over the paper of Wattig et Al.

The polydeoxyribonucleotides of E.P. 263155 were found more active than glycosaminoglycans in an experimental model of diabetic neuropathy wherein the sciatic nerve of diabetic animals was submitted to ligature.

As it will be herebelow demonstrated the compounds of reference, differently than the latter hereabove mentioned, could reestablish in said nerve an axonal transport both higher and significantly different from that of the diabetic control group. Worth mentioning is that in said experimental model have been already found efficacious drugs known in the art for their use in the therapy of diabetic neuropathies. Hence the test must be considered a valuable tool for assessing activity of compounds in the pathology.

To the above observations it must be further added that the instant claimed activity, within the low molecular weight polymers obtained by DNA depolymerization, is peculiar of the polydeoxyribonucleotides of E.P. 263155. As a matter of facts oligodeoxyribonucleotides (ref. oligodeoxyribonucleotide preparation PO.129.A of example 2) obtained by DNA according to E.P.A. 92203723.9, more in detail by depolymerizing DNA in acetate buffer for a longer reaction time than that envisaged in E.P. 263155, were found devoid of activity in the in vitro neuritogenesis test performed in an hyperglycemic medium, as further on detailed.

In conclusion the state of the art does not provide any whatsoever evidence that could lead to the instant proposed therapeutic use.

The polydeoxyribonucleotide preparation herein used was lot n. C 13.

Said compound was obtained from high molecular weight deoxyribonucleic acid according to the herebelow reported Example 1, that substantially recites example 3 of the cited E. P. 263155 whith the only difference that in the present case the heating time at the temperature of 85° C. (the second heating treatment) was of 1,30 h instead of 0,30 h.

Diabetic neuropathy, as well as hyperglycemia and large and small vessels diseases is a sign of diabetes.

Diabetic neuropathy associated with diabetes mellitus is more usually called distal sensory neuropathy.

The disease affects mainly the lower limbs, at the onset with sensory loss in the toes.

Said alterations progressively extend in a retrograde fashion to the whole lower limb. As a matter of facts in-vivo pharmacological models of experimentally induced diabetes show that for prolonged induction times nerve cellular bodies are no more able to maintain the functionality of their peripheral appendages.

In such a situation a progressive retrograde degeneration of nerve tissue sets up along the axon, leading ultimately to death of sensory neuron.

Said degeneration causes also a decrease of nerve stimuli conduction with concomitant decrease of the functionality of axonal transport.

The experimental models that have been used in this invention to demonstrate the activity in diabetic neuropathies of the polydeoxyribonucleotides obtained according to E.P. n. 263155 were, respectively, the in-vitro test of neuritogenesys resumption in SY5Y neuroblastoma cell cultures performed in a growth medium having an high concentration of glucose or galactose, and the in-vivo test of ligature of sciatic nerve which, worth incidentally observing here, is the larger of the body.

Said in-vitro test is reputed to be a reliable experimental model for assessing drug activity in diabetic neuropathies since the art evidences that substances active in this pathology are able to promote neuritogenesys in neuroblastoma cell, cultures, even in the presence of inhibitors of neurite development (W. Dimpfel "Ganglioside induced neurite formation in cultured neuroblastoma cells" in "Gangliosides in neurological and neuromuscolar function, development, and repair" M. M. Rapport and A. Gorio Editors, Raven Press; 1981:pages 119–134).

The test is substantially the same reported in the work of M. E. Yorek et Alii "Restoration of $Na^+$-$K^+$ pump activity and restoring membrane potential by myo-inositol supplementation in neuroblastoma cells chronically exposed to glucose or galactose" Diabetes 1991; 40:240–248, wherein it is demonstrated that the inhibitory effect of high concentrations in the medium of glucose or galactose (30 mM) on the growth of neuroblastoma cell cultures was totally antagonized by aldose reductase inhibitors, that are drugs used in the therapy of diabetic neuropathies.

The glucose and galactose concentrations were the same used in the foregoing paper (30 mM), and the same basically was also the culture medium used, that however in this case was added of a given quantity of polydeoxyribonucleotide lot n. C 13, or of oligodeoxyribonucleotide lot PO.129. A, in order to have in such medium concentration of the substance of $10^{-6}$ e $10^{-8}$M respectively. Each experiment was performed twice.

After one or more weeks according to the length of the experiment, (ref. Table I and II ), the culture medium was substituted with another having the same composition, from which serum had been instead omitted. In such conditions neurite growth developed.

After two days, when the neuritogenesys process was over, a quantitative evaluation of thereof results was carried out.

Neuritogenesys values of cultures treated with preparation lot C 13 or preparation PO.129.A were calculated by reference to that of the corresponding blank (glucose- or galactose-added culture not treated with the compound under test) assumed to have a value of 100.

Following Tables I and II feature the results obtained in the experiment and evidence that polydeoxyribonucleotide lot n. C 13 was able to induce neuritogenesys in the presence both of glucose and of galactose.

Worth noting is that the polymer preparation obtained with longer depolymerization time from high molecular weight DNA (compound batch n. PO.129.A ) was instead ineffective in said test (ref. Table IV).

Table III features the parameters and thereof limits of E.P. 263155, the analytical characteristics of preparation lot n. C 13 and of preparation lot n. PO.129.A. It is seen that in the case of preparation PO.129.A the values of the parameter h (reversible hyperchromicity), of specific rotation and of molar extinction referred to phosphorous were outside the limits set in the the European patent. In turn this explains that the observed difference of activity is due to a substantial chemical diversity between the two compounds.

TABLE I

Neuritogenesys resumption in SY5Y neuroblastoma cell cultures induced by polydeoxyribonucleotide lot n. C 13 (conc. $10^{-6}$ e $10^{-8}$ M) in the presence of glucose 30 mM The results herebelow shown were obtained after incubation times of one, two, three weeks respectively and calculated by reference to the blank (glucose) made up to the conventional value of 100.

| | Concentration | |
|---|---|---|
| | $10^{-6}$ M | $10^{-8}$ M |
| Glucose | (100) | (100) |
| 1st week | 144 | 202 |
| 2nd week | 168 | 182 |
| 3rd week | 132 | 113 |

TABLE II

Neuritogenesys resumption in SY5Y neuroblastoma cell cultures induced by polydeoxyribonucleotide lot n. C 13 (conc. $10^{-6}$ e $10^{-8}$ M) in the presence of galactose 30 mM. The results herebelow shown were obtained after incubation times of 1 and 2 weeks and calculated by reference to the blank (galactose) made up to the conventional value of 100.

| | Concentration | |
|---|---|---|
| | $10^{-6}$ M | $10^{-8}$ M |
| Galactose | (100) | (100) |
| 1st week | 134 | 150 |
| 2nd week | 95 | 112 |

The in-vivo test of sciatic nerve ligature in diabetic rats, as hereabove said, afforded the demonstration of the activity of polydeoxyribonucleotides of E.P. 263155 in diabetic neuropathies, since they were found able to improve significantly axonal transport in said nerve.

Said experimental model is widely used in the art. Worth herein mentioning the paper by M. Bisby "Ligature tecniques" in D. G. Weiss "Axoplasmatic Transport" Springer-Verlag Berlin Heidelberg 1982; 437–441, an that by D. B. McLean"substance P and somatostatin content and transport in vagus and sciatic nerves of the streptozocin-induced diabetic rat " Diabetes 1987; 36:390–395.

As a consequence of ligation of sciatic nerve, since axonal transport is predominantly directed from the nervous cell toward peripheral extremities (anterograde transport), a large quantity of neuropeptides accumulates in the part being comprised between the ligature and the neuron (proximal portion).

TABLE III

Parameters and thereof ranges of polydeoxyribonucleotide obtained according to the European patent n.263155 and of preparation lot n. C 13 e PO.129

| Parameters | Ranges of the patent | Lot n. C 13 | PO.129.A |
|---|---|---|---|
| Extinction Coefficient | 210–230 | 211 | 220 |
| Extinction Coefficient E230/E260 | 0,41–0,49 | 0,47 | 0,47 |
| Molar Extinction Coefficient ref. to Phosphorous | 7250–8250 | 7468 | 8343 |

TABLE III-continued

Parameters and thereof ranges of polydeoxyribonucleotide obtained according to the European patent n.263155 and of preparation lot n. C 13 e PO.129

| Parameters | Ranges of the patent | Lot n. C 13 | PO.129.A |
|---|---|---|---|
| Rotatory Power | +47°–+59° | +51,6° | +33,9° |
| Reversible Hyperchromicity | 10–20 | 18,4 | 0,7 |

TABLE IV

Neuritogenesys resumption in SY5Y neuroblastoma cell cultures induced by polydeoxyribonucleotide lot n. C 13 and by preparation PO.149.A (conc. $10^{-6}$ e $10^{-8}$ M) in the presence of glucose 30 mM after an incubation time of 1 week. Figures shown in this Table were calculated by reference to the blank (glucose) made up to the conventional value of 100.

| | Concentration | |
|---|---|---|
| | $10^{-6}$ M | $10^{-8}$ M |
| Glucose | (100) | (100) |
| Polydeoxyribonucleotide lot n. C 13 | 144 | 202 |
| Preparation PO.149.A | 112 | 109 |

In the experiment described in the instant invention axonal transport was evaluated by assaying substance P, that is contained in sensorial neurons and it is one of those neuropeptides contributing to nerve conduction.

It is known from the state of the art that in experimental diabetic neuropathy reduced levels of substance P may be put in relation also to local alteration of nervous tissue due to the pathology (Di Giulio A. M. et alii "Denervation and hyperinnervation in the nervous system of diabetic animals. II. Monoaminergic and peptidergic alterations in the diabetic encelopathy" J. Neurosci. Res. 1989; 24:362). The method used to assay substance P is described in the paper of di A.M. Di Giulio et Al. "Denervation and hyperinnervation in the nervous system of diabetic animals. I. The autonomic neuronal distrophy in the gut" J. Neurosc. Res. 1989; 24:355.

Diabetes was induced in fasted animals (rats) by subcutaneous injection of a dose of alloxane of 100 mg/Kg dissolved in a citrate—phosphate buffer O, 1 M pH 4,5 (ml 0,5).

The non diabetic control group was constituted of 6 animals, and received one subcutaneous injection of buffer only.

Seven days after injection glycemia levels were assayed by taking 180 microliters of blood from the caudal vein. To the samples 20 microliters of EDTA 5% (11 microliters EDTA/9 microliters of blood) were added.

Glycemia was assayed on the plasma, obtained after centrifugation of blood at 1500 rpm for 14 minutes at room temperature, by using the kit GOD-PAP of Boehringer Biochemia. On each sample were made two determinations.

Rats having glycemia values higher than 400 mg/dl were admitted to the experiment. With said animals three groups of six rats each were then constituted. Each animal of each group was then treated once a day intraperitoneally (500 microliters) as indicated herewith:

Control group: physiologic solution (diabetic control group).
Group A: a physiologic solution of preparation lot n. C 13 at a concentration 1 mg/Kg.
Group B—confront group: a physiologic solution of the product called in the Sigma catalogue under product number H 1642 "Heparin-like substance" (a glycosaminoglycan mixture constituted of fast moving and slow moving heparin, dermatan sulfate and chondroitin sulfate) at a concentration 1 mg/Kg.

After 5 weeks from the start of the experiment the rats were anaesthetized by intraperitoneal administration of a 0,8% pentobarbital physiologic solution and sciatic nerve ligature was made at half height of the thigh, at least at 0.8 cm from the popliteal cavity, wherein the nerve branches out. Animals were sacrificed 24 hours afterwards.

After sacrifice sciatic nerve was immediately removed and then divided into three sections, each of 2 mm length stored at –80° C.

BRIEF DESCRIPTION OF THE DRAWING

The way in which the nerve was resected is shown in FIG. 1.

Said FIGURE schematically represents a neuron (N), the sciatic nerve (horizontal channel) and the relevant peripheral extremities (E).

Figure 1:
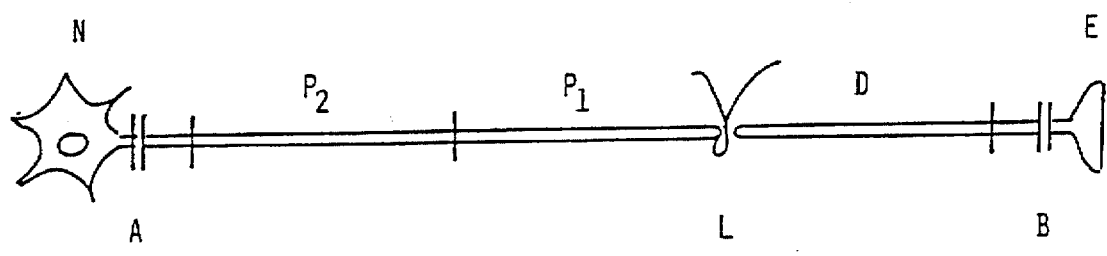

The site indicated with letter L is that of ligature.

Letters A and B (located in the correspondence of the double marked vertical lines) indicate the points wherein sciatic nerve was resected, whereas $P_1$, $P_2$ and D are the nerve segments in which the nerve was divided in order to carry out the neuropeptide assay.

More in detail $P_1$ and $P_2$ represent the proxymal segments of the sciatic nerve (on the left of the ligature) and were used for anterograde axonal transport determination, i.e. the axonal transport from the body cell to the peripheral neuron. D identifies the distal segment of sciatic nerve and thereof quantitation of substance P content afforded determination of the axonal transport directed from the peripheral extremities to the neuron cell body (retrograde transport).

The nerve segments were transferred in ice cooled polipropylene test tubes containing 1N acetic acid in a quantity by volume of 10 times the weight of tissue to be homogeneized.

From the homogenate 0.1 ml aliquots were taken for tissue protein assay. The test tubes were then placed in a boiling water bath for 8–10 minutes in order to inactivate residual peptidases. After cooling the homogenate to 4° C. for 30 minutes, centrifuging was effected at 40000× g for 10 minutes. The supernatant was recovered and then lyophilyzed.

The solid residue was dissolved in distilled water under vortexing and then centrifuged at 40000× g for 10 minutes. From the solutions were taken aliquots for quantitation of substance P by radioimmunoassay according to the method of Di Giulio et Al., Brain Res. 1985; 342:405-8.

Results are shown in Table V, wherein are given Substance P levels, as ng/mg protein, in the various segments in which left sciatic nerve had been formerly divided.

The Table shows that in the non diabetic control group anterograde axonal transport (segments $P_1$ and $P_2$) was greater and statistically different from that of diabetic control group.

In the group being treated with the polydeoxyribonucleotide obtained according to European patent n. 263155 (group A) both anterograde and retrograde (segment D) axonal transport were higher and significantly different from those corresponding of the diabetic control group.

For that it concerns in particular retrograde axonal transport (segment D) no significant difference was instead found between the control diabetic group, the non diabetic control group and the group treated with glycosaminoglycans (group B).

The Table shows also that the latter compounds in the test were barely effective, or otherwise ineffective at all, according to the nerve segments taken into consideration. The results obtained in the test with the polydeoxyribonucleotides of the European patent n. 263155 evidence that said compounds were efficacious in restoring axonal transport in sciatic nerve of diabetic animals previously submitted to ligature as hereabove formerly detailed.

Taking into account that in the art it is disclosed that in experimental models of diabetes drugs effective in diabetic neuropathy were shown to increase both nerve conduction velocity (M. Spuler et alii "Ganglioside therapy in experimental diabetic neuropathy" Arzneim.-Forsch./Drug Res. 1988; 38(II) n. 7:881–884) and the quantity of Substance P in sensory nerves (Di Giulio A. M. et Al. "Acetyl-L-carnitine prevents substance P loss in the sciatic nerve and lumbar spinal cord of diabetic animals" Int. J. Clin. Pharm. Res. 1992; XII(5/6):243–246), it must be concluded that in view of the results reported in Table V also the hereabove mentioned polydeoxyribonucleotides must be considered useful active principles for the prophylaxis and therapy of diabetic neuropathies.

TABLE V

Substance P levels (ng/mg proteins) in three segments of the sciatic nerve shown in FIG. 1. Data featured in the Table represent the average ± S.E. of six determinations.

| Experimental | Sciatic nerve | | |
|---|---|---|---|
| groups | Segment P1 | Segment P2 | Segment D |
| Non diabetic control group | *12,30 ± 0,32 | *4,69 ± 0,14 | 2,60 ± 0,16 |
| Diabetic control group | 6,67 ± 0,25 | 3,38 ± 0,11 | 2,79 ± 0,07 |
| Group treated with batch n. C13 preparation (group A) | *11,41 ± 0,18 | *7,30 ± 0,39 | *3,71 ± 0,10 |
| Group treated with glycosamino glycans (group B) | 6,11 ± 0,24 | 3,78 ± 0,09 | 2,65 ± 0,12 |

Significance of Substance P levels of a group in the confront of diabetic control group has been indicated in the Table with an asterisk.

Following Table VI demonstrates the proposition hereabove put forward at the beginning of the disclosure that within the field of neuropathies the polydeoxyribonucleotides obtained according to the hereabove mentioned European patent are active only in diabetic neuropathies.

From said Table it is in fact drawn that in the experimental model of traumatic lesion of sciatic nerve (rats), that from the art it is known to have been used to demonstrate effectiveness of drugs in acute peripheral neuropathies (ref. E.P.A. 93202089.4), the above polydeoxyribonucleotides were found inactive, giving values of substance P and met-enkefalin being quite the same than those of the lesioned control group. From the Table it is also drawn that in both groups figures are lower than the corresponding of the non lesioned control group.

TABLE VI

Experimental lesion of sciatic nerve. Quantity of Substance P of met-enkefalin (radioimmunoassay) levels in the lumbar region of the spinal cord three weeks after the lesion and following daily treatment i.p. with polydeoxyribonucleotide lot n. C 13 at at the dose of 10 mg/Kg

| | dose/g. i.p. mg/Kg | Substance P ng/mg proteins | met-enkefalin ng/mg proteins |
|---|---|---|---|
| Non lesioned Control group | — | 10,05 ± 0,24 | 0,83 ± 0,026 |
| Lesioned control group | — | 7,38 ± 0,32 | 0,39 ± 0,022 |
| Group treated with preparation lot C13 | 10 | 7,69 ± 0.30 | 0.34 ± 0.015 |

Dosage forms for parenteral use are sterile and apyrogenetic solutions containing the polydeoxyribonucleotides according to the European Patent n. 263155 stored in sealed ampoules for intramuscolar, subcutaneous or endovenous administration.

Said dosage forms may be also lyophylisates stored in sealed bottles, the solid is then extemporarily dissolved by adding the sterile aqueous solvent.

The dosage forms may be formulated with excipients already known to the practised artisan.

Dosage forms for oral administration may be tablets, gelatin capsules, coated (gastroresistant) tablets or coated gelatin capsules, granulates. The excipients are those known to the man of the art.

Daily doses for oral administration are comprised between 200 e 2000 mg, preferably between 200 e 1200 mg.

Daily doses for parenteral administration are comprised between 200 e 1400 mg, preferably between 400 e 1000 mg.

EXAMPLE 1

Preparation of polydeoxyribonucleotide according to E.P. 263155 (poly deoxyribonucleotide lot n. C 13).

90 g of high molecular weight deoxyribonucleic acid was dissolved in 1.5 liters of 3 M acetate buffer pH 4.1.

The solution was slightly warmed, filtered, and then heated at 70° C. for 4 hours. Cooling to 25° C. was afterwards effected and pH adjusted to 7.8 with 170 ml of 5N sodium hydroxide. The resulting solution was heated at 85° C. for 1.30 hours, filtered, admixed with 1.5 volumes of ethanol.

The resulting precipitate washed, dried, dehydrated with ethanol and thereafter dried under vacuum. 57 g of the compound were obtained.

EXAMPLE 2

Preparation of polydeoxyribonucleotides according to the European patent application n. 92203723.9 (Preparation n. PO.129.A ).

40 g of high molecular weight deoxyribonucleic acids were dissolved in 260 ml of distilled water and then added of g. 21.32 of sodium acetate trihydrate.

Heating was then effected on a water bath at 75° C. and 50.8 ml of 80% acetic acid were then added. Final pH was about 4.1.

After 7 hours of heating the solution was cooled at about 30° C., pH corrected at 7.8 –8 by means of 95 ml of 30% NaOH and the solution was heated at 85° C. for 1.30 h.

After subsequent cooling pH was corrected at 6,5 with few drops of 80% acetic acid and precipitation effected by adding to the solution 1.5 volumes of ethanol. After dehydration and drying gr. 35 of the compound were obtained.

We claim:

1. A method of treating or preventing the onset of a diabetic neuropathy in a patient in need of such treatment or prevention, comprising administering to the patient a polydeoxyribonucleotide of random sequence formula:

$$P_v, (dAp)_w, (dGp)_x, (dTp)_y, (dCp)_z$$

wherein $P_v$ is 1–5 phosphoric radicals, $(dAp)_w$ is 12–24 deoxyadenylic monomers, $(dGp)_x$ is 10–20 deoxyguanylic monomers, $(dTp)_y$ is 13–26 deoxythymidylic monomers, and $(dCp)_z$ is 10–20 deoxycytidylic monomers;

wherein the polydeoxyribonucleotide has:

a homogenous anodic mobility in electrophoresis, an extinction coefficient $E^{1\%}_{1\,cm}$ at $260\pm1$ nm$=220\pm10$, an extinction coefficient $E_{230}/E_{260}=0.45\pm0.04$, a molar extinction coefficient (referred to phosphorous), $\epsilon(P)=7750\pm500$, a rotary power $[\alpha]^{20°}_D=53°\pm6$, and a reversible hyperchromicity as percent in native DNA $h=15\pm5$.

2. The method of claim 1, wherein the polydeoxyribonucleotide is administered parenterally at a daily dosage of between 200 and 1400 milligrams.

3. The method of claim 1, wherein the polydeoxyribonucleotide is administered orally at a daily dosage of between 200 and 2000 milligrams.

4. The method of claim 2, wherein the daily dose is between 400 and 1000 milligrams.

5. The method of claim 3, wherein the daily dose is between 200 and 1200 milligrams.

* * * * *